United States Patent
Herlihy et al.

(10) Patent No.: US 9,428,471 B2
(45) Date of Patent: Aug. 30, 2016

(54) CYCLIC CARBAMATE COMPOUNDS USEFUL IN ENERGY-CURABLE COMPOSITIONS

(75) Inventors: Shaun Herlihy, Chatham (GB); Brian Rowatt, Maidstone (GB)

(73) Assignee: Sun Chemical B.V., Weesp (NL)

( * ) Notice: Subject to any disclaimer, the term of this patent is extended or adjusted under 35 U.S.C. 154(b) by 846 days.

(21) Appl. No.: 13/256,115

(22) PCT Filed: Mar. 11, 2010

(86) PCT No.: PCT/GB2010/000441
§ 371 (c)(1),
(2), (4) Date: Sep. 12, 2011

(87) PCT Pub. No.: WO2010/103281
PCT Pub. Date: Sep. 16, 2010

(65) Prior Publication Data
US 2012/0015159 A1   Jan. 19, 2012

Related U.S. Application Data

(60) Provisional application No. 61/159,930, filed on Mar. 13, 2009.

(51) Int. Cl.
| C09D 137/00 | (2006.01) |
| C07D 413/12 | (2006.01) |
| B32B 27/30 | (2006.01) |
| C08J 7/04 | (2006.01) |
| C08F 2/48 | (2006.01) |
| C07D 413/14 | (2006.01) |
| C09K 3/00 | (2006.01) |
| C07D 263/14 | (2006.01) |

(52) U.S. Cl.
CPC ...... *C07D 263/14* (2013.01); *Y10T 428/24802* (2015.01); *Y10T 428/31935* (2015.04)

(58) Field of Classification Search
CPC .................................................. C07D 263/14
See application file for complete search history.

(56) References Cited

U.S. PATENT DOCUMENTS

| 2,818,362 A | 12/1957 | Drechsel |
| 2,905,690 A | 9/1959 | Bakke |
| 3,268,485 A | 8/1966 | Hickner et al. |
| 4,639,472 A | 1/1987 | Green et al. |
| 4,675,374 A * | 6/1987 | Nichols ........................ 528/119 |
| 5,358,946 A * | 10/1994 | Wilde ......................... 514/235.8 |
| 7,105,646 B2 | 9/2006 | Chamberlain et al. |
| 7,933,462 B2 | 4/2011 | Ward |

FOREIGN PATENT DOCUMENTS

| EP | 1854792 | 11/2007 |
| WO | WO 95/14684 | 6/1995 |
| WO | WO 2004/078753 | 9/2004 |
| WO | WO 2005/058886 | 6/2005 |
| WO | WO 2006/104356 | 10/2006 |

OTHER PUBLICATIONS

Jean-Pierre Fouassier, "New developments in UV-curable acrylic monomers," 1993, p. 47.*
Palomo et al.: "A mild method for the alcoholysis of beta-lactams", Tetrahedrom Letters, vol. 36, No. 49, pp. 9027-9030, 1995.
Davies et al.: "Asymmetric three- and [2+1]—component conjugate addition reactions for the steroselective synthesis of polysubstituted piperidinones", Organic and bimolecular chemistry, vol. 5, No. 9, 2007,, pp. 1405-1415.
Decker et al.: "Recent Advances in UV-curing Chemistry", Journal of Coatings Technology, vol. 65, No. 819, Apr. 1993, pp. 49-57.
Decker et al. "A new method for monitoring ultra-fast photopolymerizations by real-time infrared (RTIR) spectroscopy", Makromol. Chem. 189, pp. 2381-2394, 1988.
Suga et al.: "Lewis Acid-catalyzed Michael Addition reactions of N-BOC-2-Silyloxypyrroles to 3-Acryloyl-2-Oxazolidinone", Heterocycles, vol. 71, No. 2, 2007, pp. 361-371.

* cited by examiner

*Primary Examiner* — Ian Rummel
(74) *Attorney, Agent, or Firm* — Charles C. Achkar; Ostrolenk Faber LLP

(57) ABSTRACT

Cyclic carbamate functional compounds, which are the reaction product of a cyclic carbamate having an acrylate functional group, such as N-(2-acryloyloxyethyl)oxazolidinone, with aliphatic amine compounds, said cyclic carbamate functional compounds being useful as oxygen scavengers in energy-curable compositions, such as inks, coatings and adhesives, that comprise (a) the cyclic carbamate functional compound, (b) reactive monomers and/or oligomers and, optionally, (c) a photoinitiator.

15 Claims, No Drawings

CYCLIC CARBAMATE COMPOUNDS USEFUL IN ENERGY-CURABLE COMPOSITIONS

This application is a 35 U.S.C. §371 National Stage Entry of International Application No. PCT/GB2010/000441, filed Mar. 11,2010, which claims priority to U.S. Provisional Application No. 61/159,930, filed Mar. 13,2009, both of which hereby are incorporated by reference in their entirety for all purposes as if fully set forth herein.

FIELD OF THE INVENTION

The present invention relates to energy-curable compositions, for example energy-curable inks, coatings and adhesives, and to cyclic carbamate materials useful in such compositions and to methods of making such cyclic carbamate materials.

BACKGROUND

U.S. Pat. No. 2,818,362 (American Cyanamid Co.) describes the synthesis of a new vinyl monomer, N-vinyl-2-oxazolidinone. Polymerization products made from the new monomer are also described. The polymers have been used in molding compositions or as adhesives in the production of optical devices.

U.S. Pat. No. 2,905,690 (The Dow Chemical Company) describes the synthesis of N-vinyl-X-alkyl oxazolidinone compounds using high temperature and high pressure process (Autoclave). It also describes the polymerization of these materials to produce homopolymers and copolymers using various comonomers. The use of the materials is reported as being in the dyestuffs for textiles industry.

U.S. Pat. No. 3,268,485 (The Dow Chemical Company) describes the preparation of homopolymers and copolymers of 3-(2-hydroxyethyl)-5-methyl-2-oxazolidinone acrylates/methacrylates using azo or peroxy initiators.

U.S. Pat. No. 4,639,472 (The Dow Chemical Company) describes the use of N-vinyl oxazolidinones as reactive diluents in radiation curable coatings. The coatings produced are highly oxygen permeable, have good cure properties and have good physical and resistance properties.

U.S. Pat. No. 4,933,462 (The Dow Chemical Company) describes the synthesis of 3-(2-hydroxyethyl)-2-oxazolidinones using a novel anhydrous, catalyst free process to produce highly pure products in high yield.

C. Decker and K. Moussa, *Makromol. Chem.*, 189, 2381-2394 (1988) describes a method based on IR Spectroscopy which has been developed to follow real-time photopolymerizations. The method has been used to look at photoinitiator efficiency, monomer reactivity, light intensity, film thickness and the oxygen inhibition. Various acrylate functional materials have been investigated as reactive acrylate diluents in a photopolymerisable resin and the dependence of the rate of polymerisation and the ultimate degree of conversation on the type of diluents monomer studied. A new monoacrylate oxazolidinone functional material, Acticryl CL 959 (N-(2-acrylyloxyethyl) acrylate), developed by SNPE was found to be the most efficient reactive acrylate diluents of those tested.

C. Decker and Khalil Moussa, *Journal of Coatings Technology*, 65(819), 49-57 (1993) describes the efficiency of newly developed photoinitiators and acrylic monomers by using Real Time Spectroscopy techniques to follow the kinetic profiles of various photopolymerizations. Some of the new monomers are described as being highly reactive leading to remarkable mechanical properties such as hardness, scratch resistance, flexibility and impact resistance. The monomer N-(2-acrylyloxyethyl) oxazolidinone (Acticryl CL-959 (SNPE)) has been reported here as being one of these highly reactive materials.

Lewis acid-catalyzed Michael addition reactions of N-Boc-2-silyloxypyrroles to 3-actyloyl-2-oxazolidinone, Suga, Hiroyuki; Takemoto, Haruka; Kakehi, Akikazu, *Heterocycles* (2007), 71(2), 361-371 describes the Lewis acid-catalyzed Michael addition of siloxypyrroles to acryloyloxazolidinone. A slow addition of the 2-silyloxypyrrole at −25° C. was needed to obtain good yields (77-80%).

Known compounds comprising an oxazolidinone ring compounds include:

CAS Registry Number: 1030799-93-9

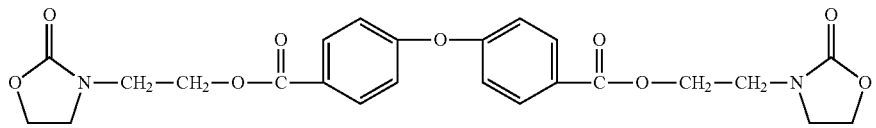 [SMILES: O=C(OCCN1CCOC1=O)c1ccc(Oc2ccc(C(=O)OCCN3CCOC3=O)cc2)cc1]

CAS Registry Number: 128276-03-9

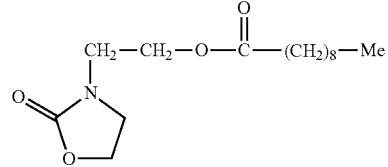

Formula: $C_{15}H_{27}N\,O_4$
CA Index Name: Decanoic acid, 2-(2-oxo-3-oxazolidinyl) ethyl ester U.S. Pat. No. 7,105,646 B2 (Sun Chemical Corporation) describes mono-and bis-azo hydrazone compounds that comprise a pyrrolinone ring for use as pigments.

Coatings, inks and adhesives based on acrylate functional raw materials can be cured in a curing process via a free radical polymerization mechanism. Most often this process is started by irradiation with actinic radiation, such as UV (ultraviolet) light, with photoinitiators present in the formulation to absorb the radiation and generate the free radical initiating species. Alternatively, the process can be initiated by irradiation with electron beam (EB) radiation. The curing process is well known to be inhibited by atmospheric oxygen such that control measures are required to reduce the effect of the oxygen inhibition and allow good curing, particularly at the surface. One method is to use a nitrogen blanket, but this is technically complex and expensive. The more usual approach is to use a blend of photoinitiator types and amine synergists in the formulation.

To those skilled in the art it is well known that free radical photoinitiators fall into two categories; cleavage and hydrogen abstraction types. When in an excited state following irradiation, cleavage photoinitiators undergo homolytic scission to form two radical fractions. Typical cleavage photoinitiators include aryl ketone and phosphine oxide photoinitiators. Cleavage photoinitiators are generally speaking more reactive, but give poorer surface curing because of oxygen inhibition, particularly in the case of phosphine oxide-type cleavage photoinitiators. Hydrogen abstraction photoinitiators typically extract a hydrogen atom from a donor molecule such as an amine synergist to form an inactive radical and a donor radical that is capable of initiating radical reactions. Typical hydrogen abstraction photoinitiators include benzophenones and thioxanthones that form stabilized inactive radicals on hydrogen abstraction. Hydrogen abstraction types only function effectively in the presence of hydrogen donors, such as amine synergists, but this mechanism makes them particularly good at combating oxygen inhibition at the surface.

Phosphine oxide-type cleavage photoinitiators are particularly suited to use in energy-curable compositions that are cured using UV radiation generated by an LED (light emitting diode) source as they absorb, and are excited by, light in the frequency range emitted by LEDs. Phosphine oxide-type cleavage photoinitiators are also particularly suited for use in clear coating and white ink compositions as they typically do not discolour the cured composition and are "non-yellowing".

SUMMARY OF THE INVENTION

The materials which are the subject of this invention are novel cyclic carbamate functional compounds made by the reaction of a cyclic carbamate compound containing a (meth)acrylate functional group, such as N-(2-acryloyloxy-ethyl) oxazolidinone, with aliphatic amine materials. This new class of materials combat oxygen inhibition by an oxygen scavenging rather than a hydrogen abstraction mechanism and are significantly more effective in doing so with the more reactive cleavage-type photoinitiators, particularly the phosphine oxide type. This allows the formulator to achieve enhanced cure speed and reduced oxygen inhibition without requiring the use of hydrogen abstraction photoinitiators in the formulation.

In a first aspect, the invention provides a cyclic carbamate compound, which contains a 5-to 7-membered cyclic carbamate ring system linked via an alkylene or polyether group to a 3-amino propionate group or 3-amino-2-methyl propionate group.

In a second aspect, the invention provides a method of preparing a cyclic carbamate compound for use in an energy-curable composition, comprising the step of reacting an aliphatic amine with (i) a cyclic carbamate having a (meth)acrylate functional group and a 5-to 7-membered cyclic carbamate ring, and, optionally (iii) a multifunctional acrylate. The cyclic carbamate compound of the first aspect of the invention may, for example, be the reaction product of the second aspect of the invention.

In a third aspect, the invention provides a cyclic carbamate compound for use in an energy-curable composition, which is the Michael addition reaction product of an aliphatic amine, a cyclic carbamate having a (meth)acrylate functional group and a 5-to 7-membered cyclic carbamate ring. The cyclic carbamate compound of the third aspect of the invention may, for example, be the reaction product of the second aspect of the invention.

In a fourth aspect, the invention provides an energy-curable composition comprising a cyclic carbamate compound of the first or third aspects of the invention or a cyclic carbamate compound produced the method of the second aspect of the invention.

In a fifth aspect, the invention provides a method of preparing an energy-curable composition, said method comprising the steps of: providing a cyclic carbamate compound, which is the reaction product of (i) a cyclic carbamate having a (meth)acrylate functional group and a 5-to 7-membered cyclic carbamate ring, (ii) an aliphatic amine, and optionally (iii) a multifunctional acrylate; and then combining the cyclic carbamate compound with at least one acrylate monomer and/or oligomers and, optionally, a photoinitiator. The energy curable composition of the fourth aspect of the invention may, for example, be the product of the method of the fifth aspect of the invention.

In a sixth aspect; the invention provides the use of a cyclic carbamate compound as described herein, for example the cyclic carbamate compound of the first or third aspects of the invention and/or the compound produced in the second aspect of the invention, as an oxygen scavenger in an energy-curable composition, such as the energy-curable composition of the fourth aspect of the invention or the energy curable composition produced in the method of the fifth aspect of the invention.

In a seventh aspect, the invention provides a method of coating or printing a substrate comprising the steps of applying an energy-curable composition of the fourth aspect of the invention to the substrate and curing the composition.

In an eighth aspect, the invention provides a coated or printed article comprising a combination of a substrate and a cured coating or printed image comprising the cyclic carbamate compound of the first or third aspects of the invention and/or a coated or printed article comprising a combination of a substrate and the energy-curable composition of the fourth aspect of the invention. The coated or printed article of the eighth aspect of the invention may, for example, be prepared according to the method of the seventh aspect of the invention.

In a ninth aspect, the invention provide a method of adhering a first article to a second article comprising the steps of applying a layer of an energy-curable composition of the fourth aspect of the invention to the first article, contacting the layer with the second article and curing the composition.

In a tenth aspect, the invention provides an object comprising a first article adhered to a second article by a layer of adhesive comprising the cyclic carbamate compound of the first or third aspects of the invention and/or a layer of the energy-curable composition of the fourth aspect of the invention.

Advantageously, the oxazolidinone derivative compounds and other cyclic carbamate compounds described herein are useful as cure boost materials, enhancing the rate and or degree of curing, by acting as oxygen scavenger agents, which lessen the oxygen inhibition of the cure of energy curable compositions.

Energy-curable compositions comprising the compound of the invention and cleavage-type photoinitiators, including phosphine oxide photoinitiators, have been found to have acceptable levels of curing, including acceptable levels of curing on the surface.

The compounds disclosed are novel compounds and represent a new class of compound for use in energy-curable compositions. Preferably, the energy-curable compositions are radiation-curable compositions such as compositions that are curable using actinic, such as UV, or EB radiation. Use of some oxazolidinone derivatives has been previously described but none that are based on Michael addition products of aliphatic amine compounds and a cyclic carbamate acrylate, such as an oxazolidinone acrylate.

DETAILED DESCRIPTION OF THE INVENTION

The term "energy-curable" refers to a composition that is curable on exposure to electromagnetic radiation, such as light, especially UV light, or electron beam (EB) radiation. Exposure to radiation typically, but not exclusively, initiates a polymerization reaction, such a free radical-mediated polymerization chain reaction. For the avoidance of doubt, solvent-based compositions in which curing is achieved primarily through the removal of a solvent, for example by evaporation, including solvent-based compositions for which radiation, such as heat, may be used to accelerate removal of the solvent, are not "energy-curable" compositions of the present invention. Preferably, the energy-curable composition of the invention is a composition curable by UV-or EB-radiation.

The term "cyclic carbamate" refers to a monocyclic ring system including a carbamate (—O—C(O)—NR—), alternatively known as an N-substituted urethane group, functional group, within the ring.

The terms "alkylene" and "alkylene group" as used herein refer to a saturated divalent alkyl radical. Unless otherwise specified, an alkylene group may be branched or straight-chain. Typically, an alkylene group will include a $C_1$-$C_8$ chain, optionally substituted with $C_1$-$C_4$ alkyl branching groups, for example methyl. An isopropylene group is an example of a $C_2$ chain with a methyl branch.

The terms "polyether" and "polyether group" refer to a group with at least two repeating alkoxy units, for example 3 or more, such as 4 or more two repeating alkoxy units. Typically, a polyether will include from 2 to 10 repeating $C_1$-$C_8$ alkoxy units, for example from 2 to 10 repeating $C_1$-$C_4$ alkoxy units, optionally substituted with $C_1$-$C_4$ alkyl units, for example methyl. A polyether linking group is a divalent polyether radical that is bonded at either end to another chemical moiety.

The term "(meth)acrylate" refers to acrylate groups, methacrylate groups and mixtures thereof.

A group that is "curable in a free radical curing reaction" is a group that is capable of forming a new chemical bond to a free radical-curable monomer or oligomers in a free radical polymerisation reaction. Examples of such groups include ethylenically unsaturated groups such as vinyl and acrylate groups.

The nitrogen atom of the 3-amino propionate group or 3-amino-2-methyl propionate group of the first aspect of the invention is advantageously bonded to at least one aliphatic group such as an alkyl, cycloalkyl, polyether or polypropylene glycol group. The 3-amino propionate group may, for example, be derived from the reaction of an acrylate functional group with an aliphatic amine. The 3-amino-2-methyl propionate group may, for example, be derived from the reaction of a methacrylate functional group with an aliphatic amine.

Suitable aliphatic amines for use in preparing the cyclic carbamate compounds of the invention include at least one secondary or primary amine group. The amine of the invention may, for example, include both primary and secondary amine groups. In one embodiment, the aliphatic amine comprises at least two reactive N—H bonds. Reactive N—H bonds are advantageously capable of undergoing Michael addition reactions with acrylates. Examples of aliphatic amines that include two reactive N—H bonds are aliphatic amines including two secondary amine groups, such as piperazine, or aliphatic amines that include a primary amine group, such as propylamine. In one aspect of the invention, the aliphatic amine may include more than two reactive N—H bonds, such as four reactive N—H bonds. Examples of aliphatic amines that include four reactive N—H bonds include aliphatic amines having two primary amine groups such as ethylene diamine.

Preferably, the aliphatic amine from which the 3-amino propionate or the 3-amino-2-methyl propionate of the first aspect of the invention is derived from, or the aliphatic amine of the second or third aspects of the invention is, a diamine. Preferably, the diamine includes two amine functional groups each individually selected from secondary and primary amine groups. The aliphatic group of the aliphatic amine is, for example an alkyl, cycloalkyl, polyether or polypropylene glycol. In one embodiment, the aliphatic amine is a diamine wherein the two amine functional groups (either primary or secondary amine functional groups) are linked by an aliphatic chain. In another embodiment, the aliphatic amine is a cyclic diamine wherein two secondary amine functional groups are linked by two aliphatic chains. Examples of suitable aliphatic amines include the Jeffamine™ polyether diamines (available from Huntsman), ethylene diamine and piperazine.

The compound of the first aspect of the invention advantageously comprises a functional group that is curable in a free radical-curing reaction. In one embodiment, the functional group that is curable in a free radical-curing reaction is an ethylenically unsaturated group. Ethylenically unsaturated groups such as vinyl groups, acrylate groups and methacrylate groups advantageously form bonds to cross-link with other ethylenically unsaturated groups in free radical-mediated polymerisation reactions. Alternatively, the functional group that is cross-linkable in a free radical curing reaction is the residue of a polyol, epoxy or urethane functional polymer. Preferably, the functional group that is curable in a free radical curing reaction is an acrylate group.

In one embodiment, the cyclic carbamate compound of the first or third aspects of the invention comprises at least one acrylate functional group. A cyclic carbamate compound comprising an acrylate functional group may, for example, be the reaction product of an aliphatic amine and a cyclic carbamate having an acrylate functional group in the presence of a multifunctional acrylate compound. Examples of suitable multifunctional acrylates include di-, tri-tetra-or higher-functional acrylates, such as 1,6-hexanediaol diacrylate (HDDA) and trimethylol propane triacrylate (TMPTA). In one embodiment, the compound of the invention comprises a unit derived from a multifunctional acrylate group. The compound of the third aspect of the invention is advantageously the reaction product of an aliphatic amine with a cyclic carbamate having both a (meth)acrylate functional group and a 5-to 7-membered cyclic carbamate ring system and also with a multifunctional acrylate. As such the compound of the third aspect of the invention advantageously includes at least one (as yet unreacted) acrylate functional group.

In one embodiment of the method of the second aspect of the invention, comprises the step of reacting an aliphatic amine with (i) a cyclic carbamate having a (meth)acrylate functional group and a 5-to 7-membered cyclic carbamate ring, and with (ii), a multifunctional acrylate. In one embodiment, the cyclic carbamate compound is prepared by reacting the cyclic carbamate compound having an acrylate functional group, with the aliphatic amine, in the presence of a multifunctional acrylate. For example, the cyclic carbamate compound having an acrylate functional group may be reacted with the aliphatic amine to provide an intermediate product which is then reacted with a multifunctional acrylate, for example in a Michael addition reaction between unreacted N—H groups in the intermediate and the acrylate groups of the multifunctional acrylate. In an alternative example, the multifunctional acrylate may be reacted with the aliphatic amine to provide an intermediate product which is then reacted with the oxazolidinone acrylate, for example in a Michael addition reaction between unreacted N—H groups in the intermediate and the acrylate groups of the oxazolidinone acrylate. Advantageously, the cyclic carbamate compound having an acrylate functional group is first reacted with the aliphatic amine to lessen the likelihood of gelled products being formed. In one aspect of the invention, the aliphatic amine has z reactive N—H bonds per molecule, wherein z is 1 or more, and the step of preparing the cyclic carbamate compound of the invention involves the reaction of less than z equivalents of the cyclic carbamate compound having an acrylate functional group with the aliphatic amine to form a compound including unreacted N—H bonds. In a further aspect of the invention, the compound including unreacted N—H bonds is reacted with a multifunctional acrylate to provide a cyclic carbamate derivative comprising acrylate functional groups. The reaction of the compound including unreacted N—H bonds with the multifunctional acrylate may be performed in a subsequent step to the formulation of the compound including unreacted N—H bonds or may be carried out in a one-pot process at the same time as or concurrently with the reaction of the cyclic carbamate compound having an acrylate functional group with the aliphatic amine. In one embodiment, the aliphatic amine has z reactive N—H bonds per molecule, wherein z is at least 2, and approximately z–1 or fewer equivalents of cyclic carbamate compound having an acrylate functional group are reacted with the aliphatic amine. In a further embodiment, the aliphatic amine has z reactive N—H bonds per molecule, wherein z is at least 3, for example 4 or more, and approximately z–2 or fewer equivalents of the cyclic carbamate compound having an acrylate functional group are reacted with the aliphatic amine. Unreacted N—H bonds may then be reacted with the multifunctional acrylate to provide a cyclic carbamate compound comprising acrylate functional groups derived from a multifunctional acrylate.

Advantageously, the compounds of the invention include one or more acrylate or other functional groups that are capable of reacting in a free radical curing reaction. Such compounds are advantageously incorporated into the cured film, for example by linking to reactive monomers and/or oligomers during radical polymerization reactions and are therefore non-migratable. The inclusion of acrylate functionality in the compound of the invention enables the compound to form bonds with acrylate monomers and/or oligomers in the polymer of the cured film. Thus, cyclic carbamate compounds comprising an acrylate functional group or other group capable reacting in a free radical curing reaction may advantageously migrate from the cured film to a lesser degree that those lacking acrylate functionality. Migration of substances from a cured composition is particularly undesirable when the cured composition is present in articles for use in food packaging.

In one embodiment, the cyclic carbamate having a (meth)acrylate group of the second or third aspects of the invention contains a 5- to 7-membered cyclic carbamate ring system linked to a (meth)acrylate functional group via an alkylene or a polyether.

In one embodiment of the first, second or third aspect of the invention, the 5- to 7-membered cyclic carbamate ring system linked to a (meth)acrylate functional group via an alkylene which is a $C_2$-$C_4$ chain substituted with from 0 to 3 methyl groups.

In one embodiment of the first, second or third aspect of the invention, the 5- to 7-membered cyclic carbamate ring system is a 5-membered, oxazolidinone ring system.

In one embodiment, the cyclic carbamate having a (meth)acrylate group of the second or third aspects of the invention is an oxazolidinone acrylate, such as an N-(2-acryloyloxyalkyl)oxazolidinone acrylate. In one embodiment the oxazolidinone acrylate is an N-(2-acrylyloxyalkyl) oxazolidinone, wherein "alkyl" refers to a $C_2$-$C_8$ straight chain, branched or cyclic alkylene, for example, $C_2$-$C_4$ chain substituted with from 1 to 3 methyl groups or a $C_2$-$C_4$ straight chain alkylene. Suitable oxazolidinone acrylates for use in preparing the cyclic carbamate compound of the invention include N-(2-acrylyloxyethyl) oxazolidinone and N-(2-acryloxypropyl) oxazolidinone.

Preferably, the nitrogen atom of the cyclic carbamate ring system is bonded to the alkylene or polyether.

In one aspect the cyclic carbamate compound of the invention is compound of the formula (I):

wherein:
$R^1$ is a moiety of the formula (II):

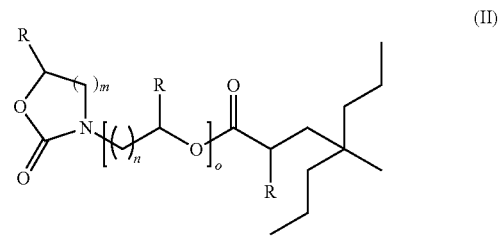

in which m is 1, 2 or 3; n is from 1 to 8; o is from 1 to 10; and each R is independently selected from H and Me;
$R^2$ is an aliphatic chain, optionally linked to a moiety of the formula (III):

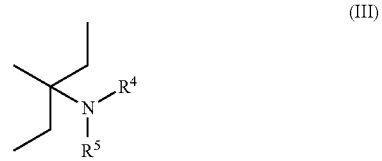

either $R^3$ is selected from:
an aliphatic group, optionally linked to a further moiety of the formula (III),
a further moiety of the formula (II), or
a unit containing an acrylate or other functional group that is curable in a free radical curing reaction;
or $R^3$ and $R^4$ together from an aliphatic chain; and $R^4$ and $R^5$ are each independently selected from:
an aliphatic group,
a further moiety of the formula (II), or
a unit containing an acrylate or other functional group that is curable in a free radical curing reaction.

In a further aspect, the cyclic carbamate compound of the invention is a compound of the formula (IV):

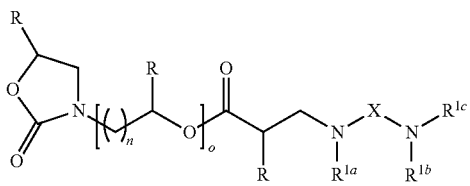

wherein:
m is 1, 2 or 3;
n is from 1 to 8;
o is from 1 to 10;
each R is independently selected from H and Me;
X is an aliphatic linker group; and
each of groups $R^{1a}$, $R^{1b}$ and $R^{1c}$ is independently selected from an aliphatic group, a moiety of the formula (II), or unit containing an acrylate or other functional group that is curable in a free radical curing reaction; or
$R^{1a}$ and $R^{1b}$ together form a further aliphatic linker group.

In one embodiment, the compound of the invention is a compound of formula (I) or (IV) in which o is 1. In a further embodiment, n is 1, 2 or 3 and o is 1. In a yet further embodiment, m=n=1, 2 or 3 and o is 1. In one embodiment, m is 1 or 2. In a further embodiment, m is 1.

In one embodiment, the compound of the invention is a compound of formula (I) or (IV) in which each R is H.

In one aspect, the compound of the invention is a compound of the formula (V):

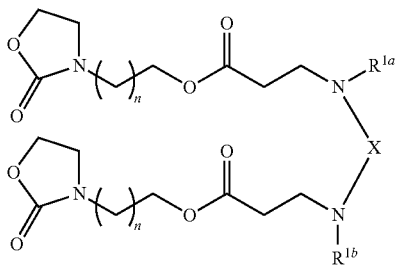

wherein
each n is independently selected from 1 to 8, for example 1, 2 or 3;
X is an aliphatic linker group; and
either $R^{1a}$ and $R^{1b}$ together form a further aliphatic linker group or $R^{1a}$ and $R^{1b}$ are each independently, selected from an aliphatic group, a moiety of the formula (II), or a unit containing an acrylate or other functional group that is curable in a free radical curing reaction.

In one embodiment, the compound of the invention is a compound of formula (I), (IV) or (V) in which X is an alkylene, such as a $C_1$-$C_8$ chain, optionally substituted with $C_1$-$C_4$ alkyl, for example methyl. In another embodiment, X is a polyether.

In one embodiment, the compound of the invention is a compound of formula (I), (IV) or (V), wherein the compound comprises at least two moieties of the formula (II).

In one embodiment, the compound of the invention is a compound of formula (I), (IV) or (V), comprising at least one functional group that is curable in a free radical curing reaction, for example at least one acrylate functional group.

In one embodiment, the compound of the invention is a compound of formula (IV) or (V), wherein each of groups $R^{1a}$, $R^{1b}$ and $R^{1c}$ (where present) is independently selected from an aliphatic group, an acrylate group or a moiety of the formula (II); or $R^{1a}$ and $R^{1b}$ together form a further aliphatic linker group. In a further embodiment of the invention, each of groups $R^{1a}$, $R^{1b}$ and $R^{1c}$ (where present) is independently selected from a straight chain, branched or cyclic $C_2$-$C_8$ alkyl group, an acrylate group or a moiety of the formula (III); or $R^{1a}$ and $R^{1b}$ together form a further aliphatic linker group. In a still yet further aspect of the invention, each of groups $R^{1a}$, $R^{1b}$ and $R^{1c}$ (where present) is independently selected from an acrylate group or a moiety of the formula (II); or $R^{1a}$ and $R^{1b}$ together form a further aliphatic linker group.

In one embodiment, the compound of the invention is a compound of formula (I) (IV) or (V) in which at least one of $R^3$, $R^4$, $R^{1a}$, $R^{1b}$ and $R^{1c}$, is a moiety derived from a multifunctional acrylate. In a further aspect of the invention, the acrylate group is a moiety of the formula (VI):

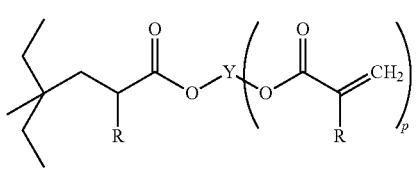

wherein Y is an aliphatic linker group; each R is independently selected from H and methyl; and p is from 1 to 8, for example from 1, 2 or 3. In one embodiment, Y is a straight chain, branched or cyclic $C_2$-$C_8$ saturated or unsaturated alkylene group, such as a straight chain, branched or cyclic $C_2$-$C_8$ saturated alkylene group, for example, a $C_2$-$C_8$ saturated alkylene group.

In one embodiment, the aliphatic group of any of $R^3$, $R^4$, $R^5$, $R^{1a}$, $R^{1b}$ and $R^{1c}$, is a straight chain, branched or cyclic $C_1$-$C_8$ alkyl group or alkenyl group. In another embodiment, the aliphatic group is a straight chain, branched or cyclic $C_1$-$C_8$ alkylene group, such as a straight chain, branched or cyclic $C_1$-$C_6$ alkylene group.

In one embodiment, the energy-curable composition of the fourth aspect of the invention is an ink, coating or adhesive. In one embodiment, the energy-curable composition is a printing ink, varnish, inkjet ink or adhesive. In one embodiment, the energy-curable composition is an ink or coating such as a printing ink (such as an offset ink), varnish or inkjet ink. In one embodiment the composition is a clear coating, for example a varnish. In another embodiment the composition is an ink, for example a printing ink, such as an offset ink, or an inkjet ink. Ink compositions of the invention advantageously further comprise a colorant, such as a pigment or dye. In a further embodiment, the energy-curable composition is a white ink. Preferably, the energy-curable composition includes at least 1 wt % of the cyclic carbamate compound of the invention, more preferably at least 2 wt % of the cyclic carbamate compound and especially at least 5 wt % of the cyclic carbamate compound. In some embodiments, the composition of the invention comprises at least 8 wt % of the cyclic carbamate compound. In one embodiment, the composition of the invention comprises less than 20 wt % of the cyclic carbamate compound, for example less than 15 wt %. In one embodiment, the composition of the invention comprises approximately 10 wt % of the cyclic carbamate compound.

In one embodiment, the energy-curable composition of the fourth aspect of the invention is curable by a free radical polymerisation mechanism. Preferably, the composition comprises at least one free radical-curable monomer or oligomer. More preferably, the compositions of the invention comprised at least one acrylate monomer or oligomer that is curable by a free radical polymerisation mechanism. Examples of suitable acrylate oligomers include aliphatic or aromatic urethane acrylates, polyether acrylates, polyester acrylates and epoxy acrylates (such as bisphenol A epoxy acrylate). Examples of suitable acrylate monomers include hexanediol diacrylate, trimethylolpropane triacrylate, di-trimethylolpropane tetraacrylate, di-pentaerythritol pentaacrylate, polyether acrylates, such as ethoxylated trimethylol propane triacrylate, glycerol propoxylate triacrylate, ethoxylated pentaerythritol tetraacrylate, and epoxy acrylates such as dianol diacrylate (the diacrylate of 2,2-bis[4-(2-hydroxyethoxy)phenyl]propane, Ebecryl 150 from UCB) and glycol diacrylates such as tripropylene glycol diacrylate.

The energy-curable compositions of the fourth aspect of the invention optionally also include one or more minor ingredients, for example, surfactants, levelling additives, photoinitiator stabilisers, wetting agents and pigment stabilisers. The latter may for example be of polyester, polyurethane or polyacrylate types, especially in the form of high molecular weight block co-polymers, and would typically be incorporated at from 2.5% to 100% by weight of the pigment. Suitable examples are Disperbyk 161 or 162 (ex BYK Chemie) or Solsperse ex Zeneca. Suitable photoinitiator stabilisers include those disclosed in EP-A-0 465 039. Suitable surfactants are preferably of the non-ionic type, for example Fluorad FC430 (ex 3M Corp.). Such surfactants (when present) are preferably included in an amount of 0.1% to 10% by weight of the total composition.

In one embodiment, the energy-curable composition of the fourth aspect of the invention is curable on exposure to actinic radiation such as light. In a further embodiment, the energy-curable composition is curable on exposure to UV radiation, for example light having a wavelength between 200 nm and 450 nm. In another embodiment the energy-curable composition is curable on exposure to near-UV radiation, for example light having a wavelength between 300 nm and 450 nm. LED UV radiation sources typically emit radiation at wavelengths within the near-UV range with 390 being a common peak emission wavelength for commercially available LED devices. In one embodiment the energy-curable composition is curable on exposure to light having a wavelength in range of from 350 to 420 nm, preferably in the range of from 360 to 405 nm and more preferably in the range of from 380 to 400 nm. In another embodiment the energy-curable composition is curable on exposure to UV radiation emitted by a UV LED light source.

In a further embodiment of the invention, the composition comprises a photoinitiator, such as a cleavage-type photoinitiator. Cleavage-type photoinitiators, also referred to as α-cleavage photoinitiators or Norrish type 1 cleavage photoinitiators, undergo cleavage into radicals on irradiation, for example irradiation with UV light. Preferably, the cleavage-type photoinitiator is activated on irradiation with light in the near-UV range as discussed above. In one embodiment, the photoinitiator is a phosphine oxide.

In an alternative embodiment, the energy-curable composition of the fourth aspect of the invention is curable on exposure to electron beam (EB) radiation.

In one embodiment, the energy-curable composition applied to a substrate in the seventh aspect of the invention is a coating, ink or adhesive composition, for example a coating or ink composition. In one embodiment, the method of the seventh aspect of the invention comprises the step of applying an energy-curable composition of the fourth aspect of the invention to a substrate and curing the composition using actinic, such as UV, or EB radiation. In a further embodiment, the composition is cured using UV radiation using a light source emitting UV radiation in the ranges discuss above with respect to the fourth aspect of the invention, for example, using a UV LED light source. In one embodiment of the seventh aspect of the invention, the energy-curable composition is applied by a printing technique, such as offset printing, ink jet printing or screen printing. In one embodiment of the method of the seventh aspect of the invention, an ink composition is applied to the substrate to form a printed image.

In one embodiment, the coated or printed article of the eighth aspect of the invention comprises a combination of a substrate and a cured layer of the energy-curable composition of the fourth aspect of the invention. The cured layer may, for example, be a coating, such as a varnish, or a printed image.

In one embodiment, of the tenth aspect of the invention, the first article is adhered to the second article by a cured layer of the energy-curable composition of the fourth aspect of the invention.

ABBREVIATIONS & MATERIALS

| | |
|---|---|
| GPTA | Glycerol propoxylate triacrylate, OTA480 (Cytec Industries) |
| HDDA | 1,6-hexanediol diacrylate, SR238 (Sartomer Europe) |
| Irgacure ™ 184 | 1-hydroxycyclohexyl phenyl ketone, a free-radical photoinitiator available from Ciba-Geigy (BASF) |
| TMPTA | trimethylolpropane triacrylate, SR351 (Sartomer Europe) |
| TPO | Darocur ™ TPO is diphenyl (2,4,6-trimethyl-benzoyl)-phosphine oxide, a free-radical photoinitiator available from Ciba-Geigy (BASF) |
| Benzophenone | Omnirad BP (IGM Resins) |
| Amine Acrylate | CN3715 Acrylated amine synergist (Sartomer Europe) |
| Epoxy Acrylate Resin | Photomer 3016 (Cognis) |
| M | molar |
| FTIR | Fourier Transform Infra Red Spectroscopy |
| $^1$H NMR | Proton Nuclear Magnetic Resonance Spectroscopy |
| $^{13}$C NMR | Carbon Nuclear Magnetic Resonance Spectroscopy |
| MS | Mass Spectroscopy |

All other chemicals, materials and reagents used in the synthesis of Oxazolidinones 1 to 6 were obtained from Sigma-Aldrich UK Ltd.

EXAMPLES OF THE INVENTION

The following examples are provided to illustrate the invention should not be construed as limiting.

Oxazolidinone Derivatives

The preparation of oxazolidinone derivatives materials of the invention using various well-known synthesis procedures such as Michael addition and esterification using acid chlorides is described below.

Oxazolidinone 1 (Intermediate): N-(2-hydroxyethyl) oxazolidinone

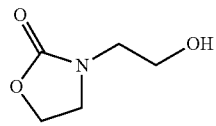

Diethanolamine, 84.0 g (0.8 moles), and dimethylcarbonate, 72.0 g (0.8 moles), were mixed in a 250 ml round bottomed flask equipped with a stirrer, condenser and temperature probe. The mixture was heated to reflux for a total of 12 hours. After this time the mixture was cooled and the side product, methanol, was removed by rotary evaporator to yield the product, 51.4 g as a low viscosity liquid.

IR: 1736 cm$^{-1}$, 3400 cm$^{-1}$; $^1$H NMR: 3.2-3.4 ppm, 3.5-3.8 ppm, 4.25-4.32 ppm; $^{13}$C NMR: 45 ppm, 46 ppm, 59 ppm, 62 ppm, 159 ppm.

Oxazolidinone 2 (Intermediate): N-(2-Acrylyloxyethyl) oxazolidinone

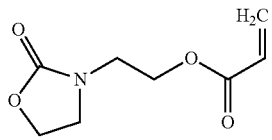

11.5 g (0.0874 moles) of N-(2-hydroxyethyl) oxazolidinone, triethylamine 8.74 g (0.08625 moles) and 50 ml of dichloromethane were mixed in a three necked round bottomed flask equipped with a temperature probe and stirrer. The contents of the flask were cooled to <5° C. using an ice/water bath. Acryloyl chloride, 7.944 g (0.0874 moles) in 50 ml of dichloromethane were then added dropwise ensuring the exotherm was controlled. The addition took approximately 150 minutes. The mixture was then allowed to stir for a further 2 hours allowing the temperature to rise to room temperature. The mixture was then filtered to remove the side products and then the organic phase was washed with 2×50 ml 0.1M hydrochloric acid, 2×50 ml 0.1M sodium hydroxide solution and 2×100 ml water. The organic layer was then dried using anhydrous magnesium sulphate and the solvent removed on a rotary evaporator to yield the oxazolidinone acrylate product, 7.02 g (43.3%) as a low viscosity liquid.

FTIR: 1752 cm$^{-1}$, 1724 cm$^{-1}$, 1638 cm$^{-1}$, 1617 cm$^{-1}$; $^1$H NMR: 3.57-3.69 ppm, 4.32-4.35 ppm, 5.85-6.41 ppm; $^{13}$C NMR: 43.3 ppm, 45 ppm, 61.6 ppm, 62.4 ppm, 127.8 ppm, 131 ppm, 158 ppm, 165 ppm; MS: mass ion 186.

Oxazolidinone 3 (Example of the invention): di[2-(2-oxo-1,3-oxazolidin-3-yl)ethyl]3-(piperazin-1,4-diyl)dipropanoate

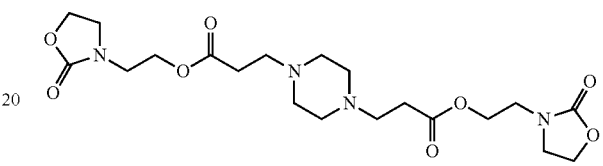

piperazine, 5 g (0.05814 moles), and 20 ml of toluene were mixed in a flask equipped with a stirrer, condenser and temperature probe. N-(2-Acrylyloxyethyl) oxazolidinone, 21.51 g (0.1163 moles), was added slowly over approximately 20 minutes, thus ensuring the exotherm was not too large. A cold water/ice bath was used to keep the temperature below 55° C. An additional 10 ml of toluene was also added with the N-(2-acrylyloxyethyl) oxazolidinone. The mixture was stirred for an additional 2 hours allowing the mixture to cool to room temperature. The solvent was then removed using the rotary evaporator to yield the piperazine dioxazolidinone product, 26 g.

FTIR: 1763 cm$^{-1}$, 1182 cm$^{-1}$; $^1$H NMR: 2.3-2.5 ppm, 3.35-3.53 ppm, 4.06-4.17 ppm; $^{13}$C NMR: 32.1 ppm, 43.4 ppm, 45.1 ppm, 52.8 ppm, 53.3 ppm, 61.5 ppm, 61.9 ppm, 158.5 ppm, 172.3 ppm; MS: mass ion 457.

Oxazolidinone 4 (Example of the Invention): Reaction Product of Ethylene Diamine, Oxazolidinone Acrylate and TMPTA

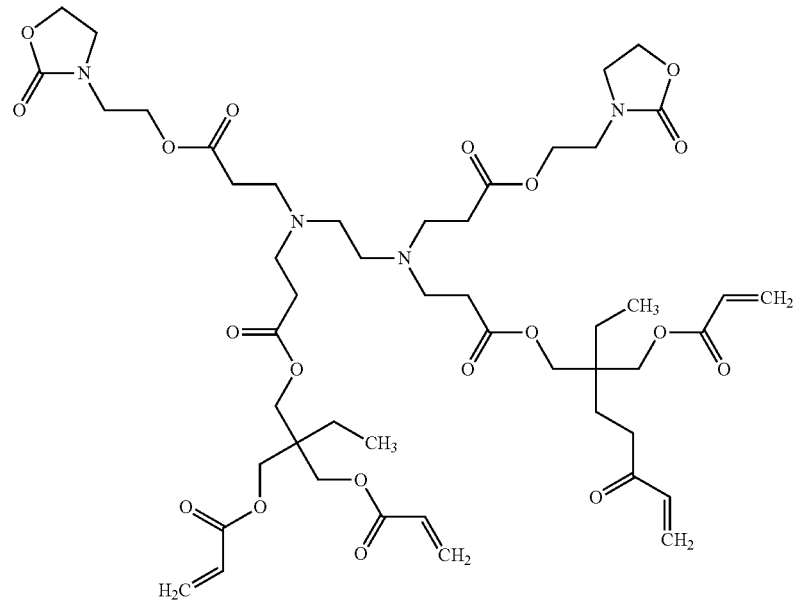 [SMILES: C=CC(=O)CCC(CC)(COC(=O)C=C)COC(=O)CCN(CCC(=O)OCCN1CCOC1=O)CCN(CCC(=O)OCCN1CCOC1=O)CCC(=O)OCC(CC)(COC(=O)C=C)COC(=O)C=C]

Ethylene diamine, 2.5 g (0.04166 moles), and 50 ml of toluene were mixed in a two necked flask fitted with a condenser, temperature probe and stirrer. N-(2-Acrylyloxyethyl) oxazolidinone, 15.42 g (0.0834 moles) was added slowly over approximately 5 minutes ensuring the exotherm was not too large. A cold water/ice bath was used to keep the temperature below 35° C. TMPTA, 49.38 g, in 40 ml of toluene was then added quickly while stirring vigorously. The mixture was then stirred vigorously for a further 2 hours and then left overnight. The solvent was then removed by rotary evaporator to yield the product, 55 g as a viscous yellow liquid.

FTIR: 1728 cm$^{-1}$, 1185 cm$^{-1}$, 1634 cm$^{-1}$, 1617 cm$^{-1}$; $^1$H NMR: 1.4-1.5 ppm, 2.2-2.7 ppm, 3.2-3.7 ppm, 3.9-4.3 ppm, 5.7-6.5 ppm; MS: mass ion 1023.

Oxazolidinone 5 (Example of the Invention):
Reaction Product of Ethylene
Diamine/Oxazolidinone Acrylate/HDDA Oxazolidinone 6 (Example of the Invention):
Reaction Product of Ethylene Diamine with
Oxazolidinone Acrylate in a Ratio of 1:4

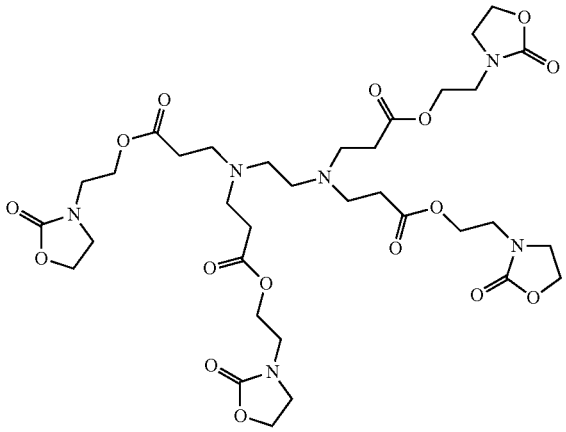

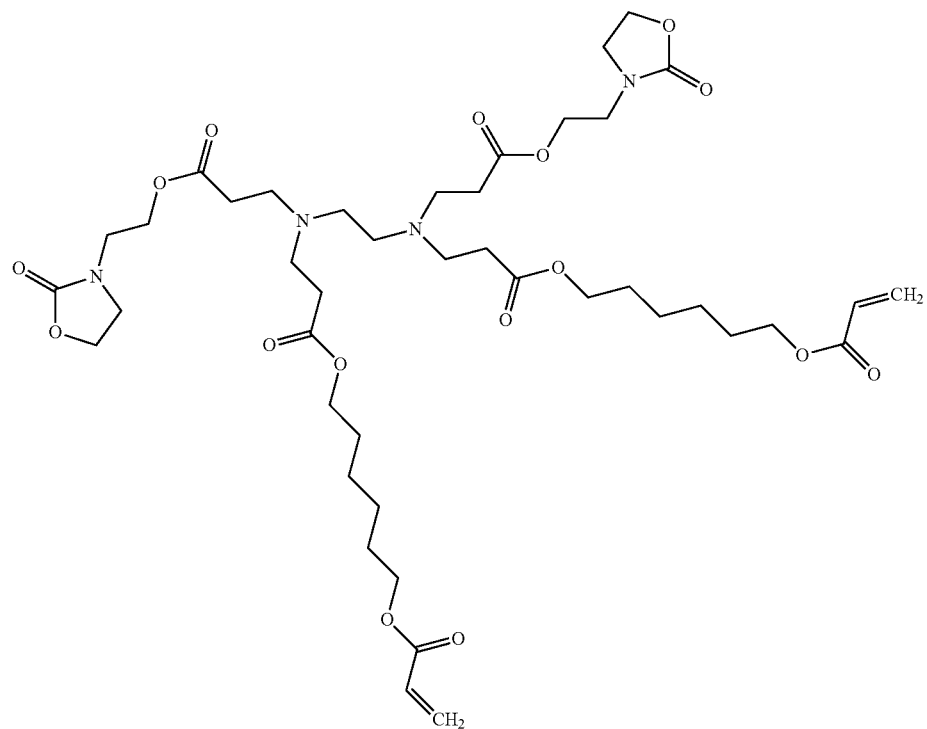 [SMILES: C=CC(=O)OCCCCCCOC(=O)CCN(CCC(=O)OCCN1CCOC1=O)CCN(CCC(=O)OCCCCCCOC(=O)C=C)CCC(=O)OCCN1CCOC1=O]

Ethylene diamine, 2.5 g (0.04166 moles), and 50 ml of toluene were mixed in a two necked flask fitted with a condenser, temperature probe and stirrer. N-(2-Acrylyloxyethyl) oxazolidinone, 15.42 g (0.0834 moles) was added slowly over approximately 5 minutes ensuring the exotherm was not too large. A cold water/ice bath was used to keep the temperature below 35° C. HDDA, 37.68 g, in 40 ml of toluene was then added quickly while stirring vigorously. The mixture was then stirred vigorously for a further 2 hours and then left overnight. The solvent was then removed by rotary evaporator to yield the product, 59 g as a viscous yellow liquid.

FTIR: 1752 cm$^{-1}$, 1724 cm$^{-1}$, 1192 cm$^{-1}$, 1634 cm$^{-1}$, 1617 cm$^{-1}$; MS: mass ion 883.

Ethylene diamine, 1.25 g (0.02083 moles) and 50 ml of toluene were mixed in a two necked flask fitted with a condenser, temperature probe and stirrer. N-(2-Acrylyloxyethyl) oxazolidinone, 15.42 g (0.0834 moles) was added slowly over approximately 5 minutes ensuring the exotherm was not too large. A cold water/ice bath was used to keep the temperature below 35° C. The mixture was then stirred vigorously for a further 2 hours and then left overnight. The solvent was then removed by rotary evaporator to yield the product, 17.8 g as a viscous yellow liquid.

FTIR: 1740 cm$^{-1}$; $^1$H NMR: 2.18-2.7 ppm, 3.2-3.7 ppm, 4.0-4.3 ppm; MS: mass ion 801.

Oxazolidinones 3 to 6 are examples of cyclic carbamate compounds of the first and third aspects of the invention.

Varnish Formulations 1 to 6

UV-curable varnishes were prepared by using each of oxazolidinone compounds 2 to 6 and the additional components shown in Table 1.

TABLE 1

| Material | % |
|---|---|
| Epoxy Acrylate Resin | 20.0 |
| Irgacure 184 | 2.0 |
| TPO | 6.0 |
| GPTA | 62.0 |
| Oxazolidinone 2-6 or control | 10.0 |
| Total | 100.0 |

Varnish formulations 2 to 5 are examples of energy-curable compositions of the fourth aspect of the invention.

The curing properties of varnish formulations 1 to 5 were evaluated by printing onto Leneta opacity charts using a No. 1 K-bar and draw down pad. The prints were passed at 80 m/min through a UV curing rig using a single 300 W/inch (approx. 120 W/cm) medium pressure mercury arc lamp operating on its full power setting. The number of passes to achieve full cure was noted. The cure was measured using the standard thumb twist test whereby a thumb is firmly applied to the cured film and twisted. Any deformation of the film or tackiness of the film or transfer of the film to the thumb is classified as a failure. Such a test is well known in the art and is, for example, described on page 74 of *Test Methods for UV and EB Curable Systems*, C. Lowe & P.K.T Oldring, SITA Technology, 1994, ISBN 0 947798 07 2. The print is considered to be fully cured when the print is dry and no thumb print or surface marking is left after the test. The cure speed of the varnishes of Examples 1 to 5 is shown in Table 2.

TABLE 2

| Varnish Formulation | Compound Evaluated in Varnish Formulation | Number of passes to cure |
|---|---|---|
| 1 (comparative) | Oxazolidinone 2 | 4 |
| 2 (example) | Oxazolidinone 3 | 2 |
| 3 (example) | Oxazolidinone 4 | 3 |
| 4 (example) | Oxazolidinone 5 | 3 |
| 5 (example) | Oxazolidinone 6 | 2 |
| 6 (comparative) | Control formulation* | 5 |

*The control formulation (varnish formulation 6) has 10% glycerol propoxylate triacrylate (GPTA) added to the components listed in Table 1 to make up to a 100 parts formulation.

The results in Table 2 above show that, despite an addition level of only 10% of an oxazolidinone functional compound, the inclusion of oxazolidinones 2 to 6, particularly oxazolidinones 3 to 6 and especially oxazolidinones 3 and 6, in the varnish boosts the cure speed of the formulation.

Varnish Formulation 7, 8 & 9

UV-curable varnishes 7, 8 and 9 were prepared using oxazolidinone compounds 2 or 3 and the additional components shown in Table 3.

TABLE 3

| Compound | % |
|---|---|
| Epoxy Acrylate Resin | 20.0 |
| Benzophenone | 7.0 |
| Amino acrylate | 8.0 |
| GPTA | 55.0 |
| Oxazolidinone 2 or 3, or control | 10.0 |
| Total | 100.0 |

Varnish formulation 8, that includes 10 wt % of oxazolidinone 3, is an example of an energy-curable composition of the fourth aspect of the invention.

The curing properties of the varnish formulations 7 to 9 were evaluated by printing the varnishes onto Leneta opacity charts using a No. 1 K-bar and drawdown pad. The prints were passed at 80 m/min through a UV curing rig using a single 300 W/inch medium pressure mercury arc lamp operating on its ½ power setting. The number of passes to achieve full cure was noted. The cure has been measured using the standard thumb twist test. The print is considered to be fully cured when the print is dry and no thumb print or surface marking is left after the test. The cure speed of the varnishes of examples 6 and 7 is shown in Table 4.

TABLE 4

| Varnish formulation | Compound Evaluated in Varnish Formulation | Number of passes to cure |
|---|---|---|
| 7 (comparative) | Oxazolidinone 2 | 2 |
| 8 (example) | Oxazolidinone 3 | 2 |
| 9 (comparative) | Control formulation* | 2 |

*The control formulation (varnish formulation 9) has an additional 10% GPTA added to make up to a 100 parts formulation.

The results in Table 4 show that the inclusion of an oxazolidinone compound in a varnish composition having an amine synergist/benzophenone hydrogen abstraction type initiator system does not affect the cure speed.

Extraction/Migration Analysis

Varnishes formulations 1, 2, 3 and 5 were printed onto untreated/uncoated foil using a No. 1 K-Bar and drawdown pad. The prints were passed at 80 m/min through a UV curing rig using a single 300 W/inch medium pressure mercury arc lamp operating on its full power setting until fully cured. The prints were then analyzed for extraction/migration using a standard procedure used for this type of analysis as described below.

The compounds were characterized by direct infusion (via a 0.5 ml/min flow of acetonitrile) APCI-LC-MS. 50 $cm^2$ of each of the prints was extracted into 20 ml of boiling toluene:acetonitrile (1:1). Gentle boiling was continued for 2 minutes. Any solvent losses were replaced by acetonitrile to maintain the solvent volume at 20 ml. The hot solvent mixture was chosen to ensure complete extraction of any uncured species. A control varnish/film with no new compound present was treated in the same manner (but 100 $cm^2$ extracted into 40 ml hot solvent to provide a relevant control matrix for subsequent LC-MS analysis). The extract from this control was used for the preparation of known concentration standards of the inventive compounds. These would be used to obtain quantitative data, for the inventive compound cured film extracts. The cooled extracts were analyzed using a direct infusion APCI method used to characterize the starting compounds. In all cases the extracted oligomer was quantified using protonated molecular ion areas from extracts and from standard solutions.

The Table 5 shows the amount of material extracted from each print and also the percentage extracted in relation to the amount of material in the varnish.

TABLE 5

| Varnish formulation analyzed | Oxazolidinone present | Amount Extracted in mg/m² | Amount Extracted as a % of compound in varnish |
|---|---|---|---|
| 1 (comparative) | 2 (comparative) | 0 | 0 |
| 2 (example) | 3 (example) | 600 | 100 |
| 3 (example) | 4 (example) | 0 | 0 |
| 5 (example) | 6 (example) | 534 | 89 |

The results indicate that the oxazolidinone compounds 3 and 6 in varnish formulations 2 and 5 were completely or almost completely extracted from the prints, whereas oxazolidinone compounds 2 and 4 that include acrylate functional groups in varnish formulations 1 and 3 were not extracted from the prints.

The results presented in Table 5 indicate that compounds with no acrylate groups fully migrate/extract from the prints but oxazolidinone compounds 2 and 4 with acrylate groups were not found to migrate/extract from the prints. The extraction of oxazolidinones 3 and 6 demonstrates that although those compounds improve cure speeds (table 2) and appear to function as oxygen scavengers they do not act as a source of abstractable hydrogens for photo initiators. If the oxazolidinone compounds were improving cure speed through functioning as photoinitiator synergists, they would be consumed in the polymerisation reaction and would not be extractable from the printed varnish composition.

The invention claimed is:

1. A cyclic carbamate compound comprising a compound of the formula (I):

$$R^3\text{-}N(R^1)\text{-}R^2 \quad (I)$$

wherein: $R^1$ is a moiety of the formula (II):

(II)

in which m is 1, 2 or 3;
n is from 1 to 8; o is from 1 to 10; and
each R is independently selected from H and methyl;
$R^2$ is an aliphatic chain, optionally linked to a moiety of the formula (III):

(III)

either $R^3$ is selected from:

an aliphatic group, optionally linked to a further moiety of the formula (III),
a further moiety of the formula (II), or
a unit containing an acrylate or other functional group that is curable in a free radical curing reaction;
or $R^3$ and $R^4$ together form an aliphatic chain; and
$R^4$ and $R^5$ are each independently selected from:
an aliphatic group,
a further moiety of the formula (II), or
a unit containing an acrylate or other functional group that is curable in a free radical curing reaction.

2. The cyclic carbamate compound of claim 1, comprising a compound of the formula (IV):

(IV)

wherein:
m is 1, 2 or 3;
n is from 1 to 8;
o is from 1 to 10;
each R is independently selected from H and Me;
X is an aliphatic linker group; and
each of groups $R^{1a}$, $R^{1b}$ and $R^{1c}$ is independently selected from an aliphatic group, a moiety of the formula (II), or a unit containing an acrylate or other functional group that is curable in a free radical curing reaction; or $R^{1a}$ and $R^{1b}$ together form a further aliphatic linker group.

3. The cyclic carbamate compound of claim 2, wherein the compound comprises at least two moieties of the formula (II).

4. The cyclic carbamate compound of claim 1, wherein the compound comprises at least two moieties of the formula (II).

5. The cyclic carbamate compound of claim 1, comprising a compound of the formula (V):

(V)

wherein
each n is independently selected from 1 to 8;
X is an aliphatic linker group; and
either $R^{1a}$ and $R^{1b}$ together form a further aliphatic linker group or $R^{1a}$ and $R^{1b}$ are each independently selected from an aliphatic group, a moiety of the formula (II), or a unit containing an acrylate or other functional group that is curable in a free radical curing reaction.

6. The cyclic carbamate compound of claim 5, comprising at least one acrylate functional group.

7. The cyclic carbamate compound of claim 1, wherein the cyclic carbamate acrylate is an N-(2-acryloyloxyalkyl) oxazolidinone.

8. An energy-curable composition comprising the cyclic carbamate compound of claim 1.

9. The energy-curable composition of claim 8, wherein the composition is curable on exposure to actinic or electron beam radiation.

10. The energy-curable composition of claim 9, wherein the composition is curable on exposure to UV radiation and wherein the composition comprises a cleavage-type photoinitiator.

11. The energy-curable composition of claim 10, wherein the photoinitiator is a phosphine oxide.

12. The energy-curable composition of claim 8, wherein the composition is in the form of an ink, coating or adhesive.

13. A method of coating or printing a substrate comprising the steps of
   (a) applying the energy-curable composition of claim 8 onto the substrate, and
   (b) curing the composition.

14. A coated or printed article comprising a combination of a substrate and the energy-curable composition of claim 8.

15. A coated or printed article comprising a combination of a substrate and a cured coating or printed image comprising the cyclic carbamate compound of claim 1.

* * * * *